(12) United States Patent
Kannan et al.

(10) Patent No.: US 6,730,793 B1
(45) Date of Patent: May 4, 2004

(54) TWO-PHOTON RESPONSIVE CHROMOPHORES CONTAINING ELECTRON ACCEPTING CORE UNITS

(75) Inventors: Ramamurthi Kannan, Cincinnati, OH (US); Loon-Seng Tan, Centerville, OH (US); Bruce A. Reinhardt, deceased, late of Tipp City, OH (US); by Erin D. Reinhardt, legal representative, Las Vegas, NV (US); by Jason A. Reinhardt, legal representative, Las Vegas, NV (US); Richard A. Vaia, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 76 days.

(21) Appl. No.: 10/171,566

(22) Filed: Jun. 13, 2002

(51) Int. Cl.$^7$ .............................................. C07D 513/02
(52) U.S. Cl. ........................ 548/150; 546/83; 548/149; 548/153; 548/156
(58) Field of Search ................... 548/150, 153, 548/156, 149; 546/83

(56) References Cited

U.S. PATENT DOCUMENTS

| | | |
|---|---|---|
| 5,770,737 A | 6/1998 | Reinhardt et al. |
| 5,859,251 A | 1/1999 | Reinhardt et al. |
| 6,100,405 A | 8/2000 | Reinhardt et al. |
| 6,300,502 B1 | 10/2001 | Kannan et al. |

Primary Examiner—Robert Gerstl
(74) Attorney, Agent, or Firm—Charles E. Bricker; Thomas L. Kundert

(57) ABSTRACT

Provided are chromophores of the formula

Q—(—L—Z)$_x$, wherein x is 2 or 3, wherein Q is selected from the group consisting of

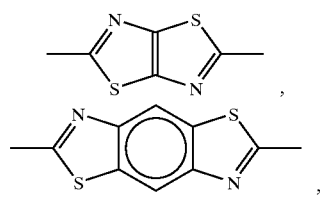

-continued

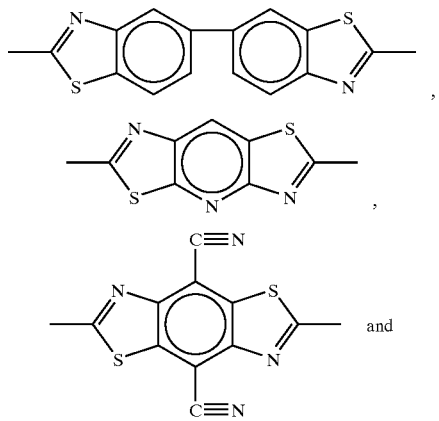

and

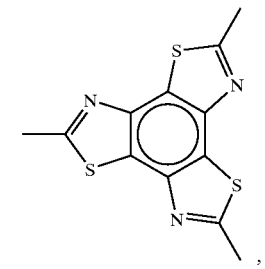

wherein L is

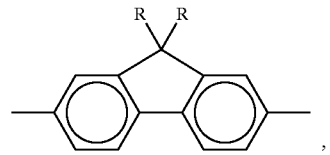

wherein R is an alkyl group having 1 to 20 carbon atoms, and wherein Z is selected from the group consisting of

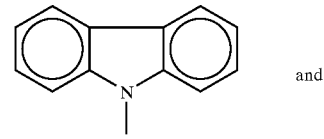

and

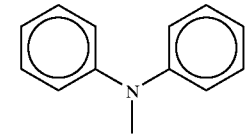

5 Claims, No Drawings

TWO-PHOTON RESPONSIVE CHROMOPHORES CONTAINING ELECTRON ACCEPTING CORE UNITS

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with very large two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (TPA), two quanta of photons may be absorbed from a single light source (degenerate TPA) or two sources of different wavelengths (non-degenerate TPA). Although multiphoton absorption processes have been known since 1931, this field remained dormant largely due to the lack of TPA-active materials with sufficiently large cross-sections. In the mid-1990s, several new classes of chromophores exhibiting very large effective TPA cross-section ($\sigma_2'$) values were reported. In conjunction with the increased availability of ultrafast high-intensity lasers, the renewed interest has not only sparked a flurry of activities in the preparation of novel dye molecules with enhanced $\sigma_2'$ values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis upconversion; (b) deeper penetration of incident light; (c) highly localized excitation allowing precision control of in-situ photochemical events in the absorbing medium, thereby minimizing undesirable activities such as photodegradation or photobleaching; (d) fluorescence when properly manipulated allows information feedback. It is anticipated that further ingenious utilization of these basic characteristics will lead to practical applications other than those already emerged in such diverse areas as fluorescence imaging, data storage, eye and sensor protection, microfabrication of microelectromechanical systems (MEMS), photodynamic therapy, etc.

In U.S. Pat. No. 5,770,737, Reinhardt et al disclose asymmetrical dyes with large two-photon absorption cross-sections and in U.S. Pat. No. 5,859,251, Reinhardt et al disclose symmetrical dyes with large two-photon absorption cross-sections. The asymmetrical dyes have the structure Acceptor-Core-Donor, and the symmetrical dyes have the structures Acceptor-Core-Acceptor and Donor-Core-Donor. In U.S. Pat. No. 6,300,502, Kannan et al disclose multi-branched TPA chromophores with 4, 5 or 6 branches from the core, thereby increasing the number density, i.e., the number of TPA-active subunits within the individual chromophore molecules.

Accordingly, it is an object of the present invention to provide new multi-branched TPA chromophores.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided novel TPA chromophores having the structure

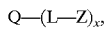

wherein x is 2 or 3, wherein Q is selected from the group consisting of

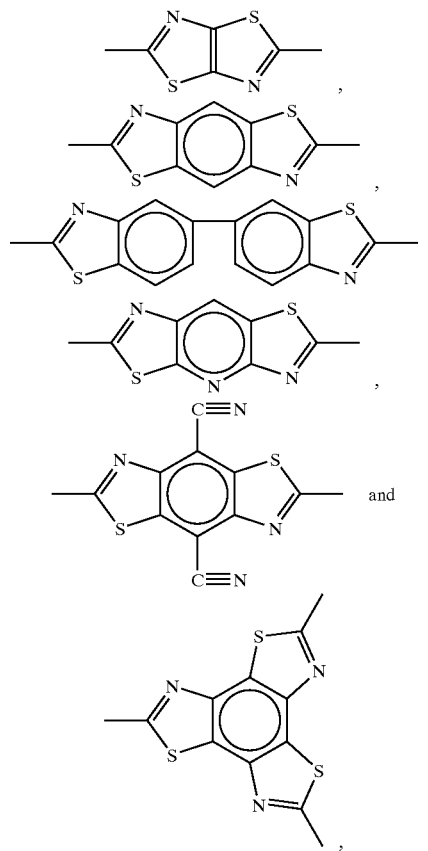

and wherein L is

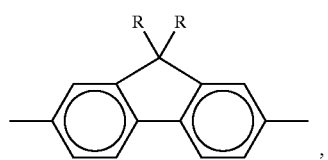

wherein R is an alkyl group having 1 to 20 carbon atoms, and wherein Z is selected from the group consisting of

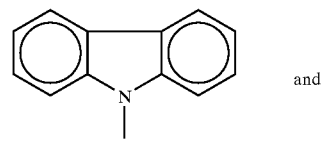

and

-continued

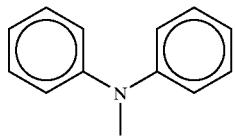

The chromophores of this invention can be synthesized following the procedures given in the following Examples which illustrate the invention:

EXAMPLE 1

2,7-Dibromo-9,9-didecyifluorene

A mixture of 2,7-dibromofluorene (64.8 g, 0.20 mol potassium iodide (3.0 g, 0.018 mol), finely powdered KOH (56.0 g, 1 mol), and DMSO (150 mL) was mechanically stirred under nitrogen in a three-necked round-bottom flask. The flask was cooled in an ice water bath before adding four batches of the bromoalkyl (90 mL. 95.94 g, 0.434 mol). After each addition, the internal temperature rose sharply. Once the last aliquot was completed, the reaction was stirred for 4 hours at room temperature before water (200 mL) was added. The solid was filtered off and dried in a desiccator equipped with $P_2O_5$ under vacuum for 16 hours. The crude product was recrystallized from ethanol to produce 2,7-dibromo-9,9-didecylfluorene as white crystals (m.p. 40–41° C.) in 92.7% yield. Mass Spec. m/z 602,604,606 ($M^+$), 461,463,465 ($M-C_{10}H_{21}$), 382,384 (461-Br). Anal. Calcd for $C_{33}H_{48}Br_2$: C, 65.56%; H, 8.00%; Br, 26.44%. Found: C, 64.99%; H, 8.21%; Br, 27.25%.

EXAMPLE 2

7-Bromo-9,9-didecylfluorene-2-carbaldehyde

To a solution of 2,7-dibromo-9,9-didecylfluorene (95.5 g, 0.158 mol) in terahydrofuran (THF, 375 mL), cooled In a dry-ice acetone bath, a 1.6 M solution of n-butyl lithium in hexanes (100 mL) was added over a period of 25 minutes. After stirring for 30 minutes a solution of dimethylforamide (DMF, 23 mL) in THF (25 ml) was added and the mixture was stirred for 1 hour in the cooling bath. After the mixture had been warmed to 0° C., hydrochloric acid (1:1, 50 mL) was added, diluted with toluene and the organic phase was separated, dried and concentrated. The residue that remained after rotary evaporation of the solvents was chromatographed over 600 g of silica gel. After elution with hexanes, the column was eluted with 1:3 toluene-hexane to obtain the aldehyde, 70.5 g, (81% yield), m.p. 45–47° C. A sample was recrystallized from a mixture of isopropanol and methanol, m.p. 49–49.5° C. IR (KBr; $cm^{-1}$): 2922, 2853, 1696 (C=O), 1605, 1459. Anal. Calcd. for $C_{34}H_{49}BrO$: C, 73.76%; H, 8.92%; Br, 14.43%. Found: C, 73.75%; H, 8.86%; Br, 14.64%.

EXAMPLE 3

2,5-Bis(7-bromo-9,9-didecylfluoren-2-yl)-1,3-thiazolo(5,4-d)1,3-thiazole

Run A

A mixture of 7-bromo-9,9-didecylfluorene-2carbaldehyde (example 2; 6.6 g, 12 mmol), dithiooxamide (rubeanic acid, 0.6 g, 5 mmol) and DMSO (4 mL) was heated in an oil-bath to a bath temperature of 190° C., held 1 hour and poured onto water. The mixture was extracted into toluene (200 mL). The toluene extract was washed with water, dried and concentrated. The resulting residue was chromatographed over alumina to get a mixture of product containing the aldehyde product. The mixture was rechromatographed over silica gel, and elution with toluene gave 0.9 g (15% yield) of the product which was recrystallized from a mixture of heptane and hexanes to get pure product 0.6 g, (10% yield), m.p. 150.8–152.7° C. Mass Spec.(m/z): 1186, 1188, 1190 ($M^+$). Anal. Calcd. for $C_{70}H_{96}Br_2N_2S_2$: C, 70.68%; H, 8.14%; N, 2.36%; S, 5.39%; Br, 13.44%. Found: C, 70.69%; H, 8.22%; N, 2.07%; S, 5.31%; Br, 13.67%.

Run B

A mixture of 7-bromo-9,9-didecylfluorene-2-carbaldehyde (example 2; 8.3 g, 15 mmol), dithiooxamide (1.0 g, 8.3 mmol), DMF (15 mL) and toluene (15 mL) was heated to reflux (124° C.), and over an hour toluene was distilled off to raise the reaction temperature to 150° C. During this time there was evolved 52 mL of a gas (31% of theory on dithiooxamide). The reaction was worked up by extracting the product with toluene. Column chromatography of the extract resulted in 4.49 g (50%) of the product in two crops, m.p. 151–53° C. and m.p. 147–49° C. The same reaction furnished another product in the earlier fractions from the column chromatography, 0.2 g (2.5%), m.p. 108–11° C., identified as a 7,7'-bis(9,9-didecylfluorene)-1,2-ethane. Mass Spec (m/z): 1072, 1074, 1076 ($M^+$). Anal. Calcd. for $C_{70}H_{96}Br_2$: C, 75.95%; H, 9.19%; Br, 14.86%. Found: C, 75.88%; H, 9.29%; Br 14.81%.

Three more runs of the reaction were conducted in a similar manner with following conditions and yields:

(1) aldehyde to dithioxoamide molar ratio, 2:1; xylene/DMF 1:1 (vv); 140–150° C.; 3 hours to get 30% yield of the product.

(2) same molar ratio of reactants; DMAc/xylene 1:1 (v/v); 142–165° C.; 6 hours to get 45% yield of the product.

(3) same molar ratio of reactants plus 1.3 equivalents of elemental sulfur with respect to dithiooxamide; DMAC/toluene 1:1; 125–160° C., 5 hours to get 24% yield of the thiazolothiazole product and 1.3% yield of 7,7'-bis(9,9-didecylfluorene)-1,2-ethane.

EXAMPLE 4

2,5-Bis(7-carbazol-9-yl-9,9-didecylfluoren-2-yl)-1, 3-thiazolo(5,4d)1,3-thiazole (AF-387)

A mixture of 2,5-bis(7-bromo-9,9-didecylfluoren-2-yl)-1, 3-thiazolo(5,4-d)1,3-thiazole (example 3; 5.959, 5 mmol), carbazole (3.349, 20 mmol), potassium carbonate (3.39, 23.9 mmol), copper bronze (1.29, 18.9 mmol) copper(I) iodide (1.189, 6.2 mmol), N,N-dimethylacetamide (30 mL) and xylenes (30 mL) was heated under nitrogen allowing xylene (25 mL) to distill off to reach a reaction temperature range of 162–167° C. The mixture was maintained at this temperature range for 34 hours, and was then allowed to cool to room temperature, the mixture was filtered and the inorganic solids were washed with toluene. The filtrate was washed with water, dried and concentrated. The residue was adsorbed on alumina (100 g), and then transferred to a column of alumina (350 g). Elution with 1:1 toluene-heptane gave a mixture of the desired product and carbazole, 6.24 g. This mixture was heated to reflux in ethanol (200 mL) for 1 hour and cooled to get the product free of carbazole, 3.4 g (50% yield), m.p. 162.1–165° C. On recrystallization from toluene-ethanol (1:2) raised the m.p. to 163.4–165.7° C. Mass Spec (m/z): 1362 ($M^+$). IR (KBr, $cm^{-1}$) 3053, 2923, 2851, 1604, 1449, 1333, 1227, 818, 742, 722, 667. Anal. Calcd. for $C_{94}H_{112}N_4S_2$: C, 82.89%; H, 8.29%; N, 4.11%; S, 4.71%. Found: C, 82.78%; H, 8.29%; N, 3.93%; S, 4.66%.

EXAMPLE 5

(7-{5-(7-(diphenylamino)-9,9-didecylfluoren-2-yl)(1,3-thiazolo(5,4-d)1,3-thiazole-2-yl)}-9,9-didecylfluoren-2-yl)diphenylamine (AF-389)

A mixture of 2,5-bis(7-bromo-9,9-didecylfluoren-2-yl)-1,3-thiazolo(5,4d)1,3-thiazole (example 3; 5.95g, 5 mmol), diphenylamine (2.69 g, 15.9 mmol), and toluene (80 mL) was azeotroped dry under nitrogen and cooled. Bis(dibenzylidene acetone)palladium(0) (0.078 g, 0.14 mmol), bis(diphenylphosphino)ferrocene (78 mg, 0.14 mmol), and sodium t-butoxide (2.07 g, 21.5 mmol) were then added, and the mixture was heated to 100° C., and held for 20 hours. After cooling, the reaction was diluted with toluene and water. The toluene phase was dried and concentrated. The resulting residue was chromatographed over alumina (350 g), and elution with heptane-toluene (3:1) gave the diphenylamine-contaminated product, which was reslurried in ethanol to remove the diphenylamine. The product, 5.48 g (80% yield), m.p. 155.9–157.8° C. was recrystallized successively three times to produce analytically pure sample, m.p. 158.2–160.1° C. Mass Spec. (m/z): 1364 (M$^+$). IR (KBr, cm$^{-1}$): 3035, 2923,2851,1591, 1489, 1431, 1275, 752 and 694. Anal. Calcd. for $C_{94}H_{116}N_4S_2$: C, 82.65%; H, 8.561%; N, 4.10%; S, 4.69%. Found: C, 82.48%; H, 8.71%; N, 3.96%; S, 4.78%.

EXAMPLE 6

2-Bromofluorene

To a solution of fluorene (16.6 g, 0.1 mol), in propylene carbonate (125 mL), at 60° C., N-bromosuccinimide (17.8 g, 0.1 mol) was added in one portion, and the mixture was allowed to cool over a period of 1 hour. The solids separated on dilution with water (2 L), were collected, dissolved in toluene (250 mL), and the toluene solution was washed with water. The solids left after concentration were recrystallized from ethanol-water, 23.3 g (95% yield), m.p. 95.6–101.3° C. Mass Spec. (m/z):322, 324, 326 (M$^+$ dibromo), 244, 246 (M$^+$).

EXAMPLE 7

2-Bromo-7-iodofluorene

A mixture of 2-bromofluorene (12.61 g, 50 mmol), acetic acid (125 mL), water (9 mL), concentrated sulfuric acid (4 mL), iodine (5.1 g, 20.1 mmol) and iodic acid (2.2 g, 12.5 mmol) was heated at 80–90° C. for 2 hours, cooled and filtered. The solids were washed with acetic acid (100 mL) and water (500 mL), to get the product 14.7 g (79% yield), m.p. 179–185° C. Mass Spec. (m/z): 418 (M$^+$ diiodo), 370, 372 (M+iodobromo), 322, 324, 326 (M$^+$ dibromo).

EXAMPLE 8

2-Bromo-7-iodo-9,9-didecylfluorene

To a mechanically stirred mixture of 7-iodo-2-bromofluorene (example 2; 41.34 g, 0.1 114 mol), DMSO (100 mL), potassium iodide (1.79 g), and powdered potassium hydroxide (28 g) cooled in a cold water bath, 1-bromodecane (53 mL) was added dropwise, and the mixture was stirred for 24 hours. The oil that separated on dilution with water, was extracted with toluene. Toluene extract was washed with water, dried and concentrated. The residual oil was passed through a column of 300 g alumina. Elution with 900 mL hexanes gave the product as an oil, 65 g. This was left in 200 mL of isopropanola when the product solidified, 58.63 g (81% yield), m.p. 43–45° C. Mass Spec. (m/z): 698 (M$^+$ diiodo), 650, 652 (M$^+$).

EXAMPLE 9

(7-Bromo-9,9-didecyl-fluoren-2-yl)diphenylamine

A mixture of 2-bromo-7-iodo-9,9-didecylfluorene (52.13 g, 0.08 mol), diphenylamine (15.6 g, 0.0922 mol, 1.152 eq), potassium carbonate (25.5 g, 0.1844 mol), TDA-1 (5 mL), copper bronze (3.0 g, 0.05 g atom) and xylenes (75 mL) was brought to reflux, and 35 ml, of xylenes were distilled off to reach a reaction temperature of 160° C. The reaction was maintained at this temperature for 18 hours. Some more solvent was distilled off to reach a reaction temperature of 175° C., where the reaction was held for additional 6 hours. The mixture was then cooled, diluted with 100 mL toluene, filtered, the filtrate was concentrated, and the residue was transferred to a column of 600 g of silica gel. Elution with 750 mL hexanes returned a mixture of dibromo and bromoiodo fluorenes as an oil, 10.3 g. Elution with heptane-toluene, 1:1 gave the product, 33.48 g (61% yield, 77% yield on consumed bromoiodo fluorene), m.p. 66.8–69.2° C. Mass Spec. (m/z): 691, 693 (M$^+$).

EXAMPLE 10

7-(diphenylamino)-9,9-didecylfluorene-2-carbaldehyde

To a solution of (7-bromo-9,9-didecylfluoren-2-yl)diphenylamine (34.6 g, 0.05 mol) in THF (200 mL), cooled to less than −50° C., a solution of n-butyllithium in hexanes (1.6M, 45 mL, 0.072 mol) was added over 15 minutes. After 30 minutes, a solution of DMF (7.5 mL, 0.097 mol) in THF (40 mL) was added, and after 1 hour, the temperature was allowed to rise to 0° C. The mixture was cooled in an ice bath, and treated with dilute hydrochloric acid (7.5 mL conc. HCl mixed with 60 mL water). After dilution with toluene (200 mL), the organic phase was washed with water, aqueous sodium bicarbonate, and saturated sodium chloride solution, dried and concentrated. The residue was chromatographed over 500 g of silica gel. Elution with 20% toluene-heptane and after removal of solvent, the product, which was initially obtained as a glassy solid, on standing with methanol (150 mL), crystallized into yellow solids, 28.2 g, (88% yield), m.p. 77–78.5° C. Anal. Calcd. for $C_{46}H_{59}NO$: C, 86.06%; H, 9.26%; N, 2.18%. Found: C, 85.81%; H, 9.49%; N, 2.10%. $^1$H NMR (270 MHz; CDCl$_3$, ppm): 0.61–0.65 (broad), 0.83, 0.85, 0.88 (triplet), 1.05–1.29 (complex, broad), 1.80–2.00 (complex multiplet), decyl protons, 20H; 7.02, 7.03, 7.04, 7.05, 7.06, 7.07, 7.12,, 7.15, 7.24, 7.26, 7.29, 7.59, 7.62, 7.69, 7.72, 7.80, 7.82, 7.83 (complex multiplets, aromatic protons, 16H); 10.02 (singlet, CHO proton, 1H). $^{13}$C-NMR (CDCl$_3$, noise-decoupled, ppm): 14.11, 22.66, 23.84, 29.11, 29.29, 29.55, 29.92,31.88, 40.03, 55.15 (sp$^3$ carbons); 118.21, 119.11, 121.70, 122.82, 123.11, 123.31, 124.38, 129.30, 130.83, 134.02, 134.51, 147.49, 147.64, 148.85, 151.30, 153.69 (sp$^2$ carbons); 192.19 (sp$^2$ carbon of CHO moiety).

EXAMPLE 11

(7-(6-(7-(diphenylamino)-9,9-diethylfluoren-2-yl)(1,3-thiazolo(5,4-f)benzothiazol-2-yl))-9,9-diethylfluoren-2-yl)diphenylamine (AF-388)

A mixture of the 7-(diphenylamino)-9,9didecylfluorene-2-carbaldehyde (example 10; 3.2 g, 5 mmol), 2,5- diaminobenzene-1,4-dithiol dihydrochloride, (0.62 g, 3.6 mmol), tri-n-butylamine (2 mL), and DMSO (15 mL) was held at 180–190° C. for 1 hour, in an atmosphere of nitrogen. The resultant reaction mixture was cooled, diluted with toluene, and the solution was washed with water, and dried. The residue left on concentration, was chromatographed over alumina. Elution with 1:1 (v/v) toluene-heptane gave the product, 2.01 g, (58% yield), m.p. 179.9–182.8° C. Recrystallizations from toluene-heptane raised the m.p. to 185.9–188.3° C. Low resolution FAB mass spectrum, m/z 1416.2 (M$^+$). Anal. Calcd. for $C_{98}H_{118}N_4S_2$; C, 83.12%; H, 8.40%; N, 3.96%; S, 4.52%. Found: C, 82.91%; H, 8.32%; N, 3.77%; S, 4.54%.

EXAMPLE 12

(7-(6-{2-(7-(diphenylamino)-9,9-diethylfluoren-2-yl) benzothiazol-6-yl}benzothiazol-2-yl)-9,9-diethylfluoren-2-yl)diphenylamine (AF-430)

A mixture of 7-(diphenylamino)-9,9-didecylfluorene-2-carbaldehyde (example 10; 3.2 g, 5 mmol), 3,3'-dimercaptobenzidine dihydrochloride (1.05 g, 3.56 mmol), dimethyl sufoxide (DMSO) (15 mL), and tributylamine (2 mL), was heated under nitrogen to 190° C., and kept at this temperature for 3 hours. The reaction mixture after cooling to room temperature, was diluted with water, toluene and ethyl acetate (1:1), and the organic phase was dried over magnesium sulfate and concentrated. The residue was chromatographed over a column of alumina and the desired product was eluted with 1:1 toluene-heptane; 1.94 g, (52% Yield), m.p. 191.8–193.1° C. LRFAB mass spec. m/z. 1492.2 (M$^+$). Anal. Calcd. for $C_{52}H_{61}N_2S$: C, 83.71%; H, 8.24%; N, 3.76%; S, 4.29%. Found: C, 83.52%; H, 8.28%; N, 3.65%; S 4.29%.

The TPA values of the chromophores are shown Table 1.

TABLE 1

| Chromphore | $\lambda_{max}$ (nm) Linear Abs. | β cm/GW at 0.2 mol/L | $\sigma_2$' (x $10^{-48}$ cm$^4$·sec ph·molecule) | $\sigma_2$'/MW (x $10^{-50}$ cm$^4$·sec·mole ph·molecule·g) |
|---|---|---|---|---|
| AF-387 | 411 | 2.8 | 61.2 | 4.5 |
| AF-388 | 442 | 11.4 | 234.3 | 16.2 |
| AF-389 | 437 | 28.3 | 584.0 | 42.8 |
| AF-430 | 410 | 6.2 | 127.3 | 8.5 |

Having thus described exemplary embodiments of the present invention, it should be noted by those skilled in the art that the disclosures herein are exemplary only and that alternatives, adaptations and modifications may be made within the scope of the present invention.

We claim:

1. A chromophore of the formula

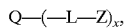

wherein x is 2 or 3, wherein Q is selected from the group consisting of

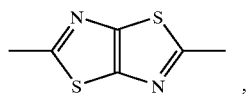

-continued

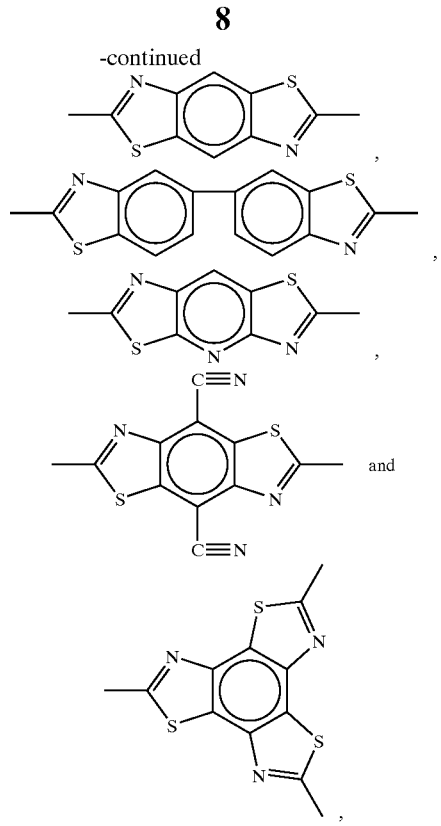

and wherein L is

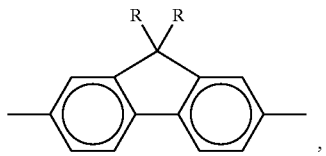

wherein R is an alkyl group having 1 to 20 carbon atoms, and wherein Z is selected from the group consisting of

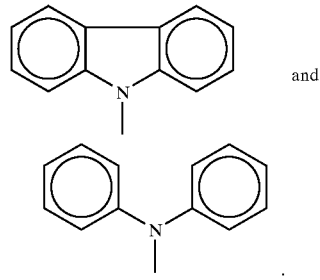

2. The chromophore of claim 1 wherein Q is

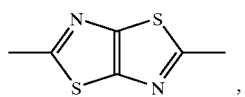

R is n—$C_{10}H_{21}$ and Z is
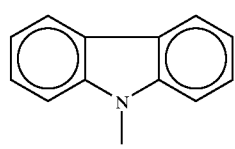
.
3. The chromophore of claim 1 wherein Q is
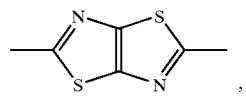
,
R is n—$C_{10}H_{21}$ and Z is
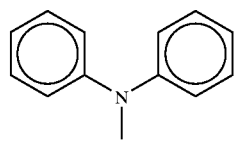
.
4. The chromophore of claim 1 wherein Q is
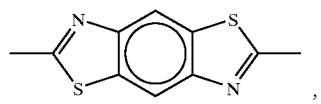
,
R is n—$C_{10}H_{21}$ and Z is
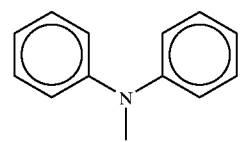
.
5. The chromophore of claim 1 wherein Q is
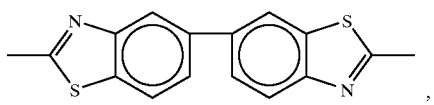
,
R is n—$C_{10}H_{21}$ and Z is
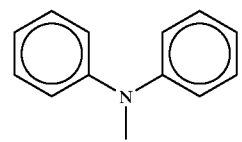
.
* * * * *